United States Patent [19]

Girard et al.

[11] Patent Number: 5,447,949

[45] Date of Patent: Sep. 5, 1995

[54] N-(HETEROARYL) IMIDAZOLYL-ALKENOIC ACIDS HAVING ANGIOTENSION II RECEPTOR ANTAGONIST ACTIVITY

[75] Inventors: Gerald R. Girard, Bensalem; David T. Hill, North Wales; Joseph Weinstock, Phoenixville, all of Pa.

[73] Assignee: SmithKline Beecham Corporation, Philadelphia, Pa.

[21] Appl. No.: 150,018

[22] PCT Filed: May 14, 1992

[86] PCT No.: PCT/US92/04071

§ 371 Date: Nov. 15, 1993

§ 102(e) Date: Nov. 15, 1993

[87] PCT Pub. No.: WO92/20651

PCT Pub. Date: Nov. 26, 1992

[30] Foreign Application Priority Data

May 15, 1991 [GB] United Kingdom ............. 9110532

[51] Int. Cl.$^6$ ............. A61K 31/415; A61K 31/44; C07D 401/14; C07D 409/14; C07D 405/14
[52] U.S. Cl. ............. 514/397; 514/341; 546/278; 548/251; 548/252; 548/253; 548/315.1; 548/315.4
[58] Field of Search ............. 548/315.1, 315.4, 251, 548/252, 253, 315.4; 514/397, 341; 546/278

[56] References Cited

U.S. PATENT DOCUMENTS

| 4,006,137 | 2/1977 | Haugwitz et al. | 548/315.1 X |
|---|---|---|---|
| 4,987,146 | 1/1991 | Rohde et al. | 514/397 |
| 5,177,096 | 1/1993 | Keenan et al. | 514/381 |
| 5,185,351 | 2/1993 | Finkelstein et al. | 514/341 |
| 5,198,438 | 3/1993 | Allen et al. | 514/235.8 |
| 5,234,917 | 8/1993 | Finkelstein et al. | 514/397 |
| 5,248,689 | 9/1993 | Girard et al. | 514/397 |
| 5,312,828 | 5/1994 | Finkelstein et al. | 514/381 |

FOREIGN PATENT DOCUMENTS

| 0218398 | 4/1987 | European Pat. Off. | 548/315.1 |
|---|---|---|---|
| 0373542 | 6/1990 | European Pat. Off. | 548/315.1 |
| 0403159 | 12/1990 | European Pat. Off. | 548/315.1 |
| 0425211 | 5/1991 | European Pat. Off. | 548/315.1 |

OTHER PUBLICATIONS

Weinstock et al, J. Med. Chem., vol. 34, pp. 1514–1517 (1991).

*Primary Examiner*—Floyd D. Higel
*Attorney, Agent, or Firm*—Mary E. McCarthy; Stephen Venetianer; Edward T. Lentz

[57] ABSTRACT

Angiotensin II receptor antagonists having the formula:

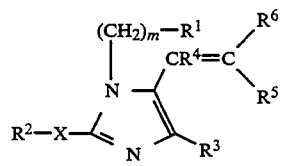

which are useful in regulating hypertension and in the treatment of congestive heart failure, renal failure, and glaucoma, pharmaceutical compositions including these antagonists, and methods of using these compounds to produce angiotensin II receptor antagonism in mammals.

10 Claims, No Drawings

N-(HETEROARYL) IMIDAZOLYL-ALKENOIC ACIDS HAVING ANGIOTENSION II RECEPTOR ANTAGONIST ACTIVITY

This application is a 371 of PCT/US92/04071 filed May 14, 1992.

The present invention relates to new N-(heteroaryl)-imidazolyl-alkenoic acids which are angiotensin II receptor antagonists and are useful in regulating hypertension induced or exacerbated by angiotensin II, and in the treatment of congestive heart failure, renal failure, and glaucoma. This invention also relates to pharmaceutical compositions containing these compounds and methods for using these compounds as antagonists of angiotensin II, as antihypertensive agents and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, exerts stimulation on the release of aldosterone from the adrenal cortex. Therefore, the renin-angiotensin system, by virtue of its participation in the control of renal sodium handling, plays an important role in cardiovascular hemeostasis.

Interruption of the renin-angiotensin system with converting enzyme inhibitors, such as captopril, has proved to be clinically useful in the treatment of hypertension and congestive heart failure (Abrams, W. B., et al., (1984), *Federation Proc.*, 43, 1314). The most direct approach towards inhibition of the renin-angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas. Pharmacol.*, 6, S176). In addition, recent animal studies suggest that inhibition of the renin-angiotensin system may be beneficial in halting or slowing the progression of chronic renal failure (Anderson, S., et al., (1985), *J. Clin. Invest.,* 76, 612). Also, a recent patent application (South African Patent Application No. 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin induced hypertension, congestive heart failure, renal failure and other disorders attributed to the actions of AII. When compounds of this invention are administered to mammals, the elevated blood pressure due to AII is reduced and other manifestations based on AII intercession are minimized and controlled. Compounds of this invention are also expected to exhibit diuretic activity.

Recognition of the importance of blocking and inhibiting the actions of AII has stimulated other efforts to synthesize antagonists of AII. The following references have disclosed imidazole derivatives which are described as having AII blocking activity and useful as hypotensive agents.

Furukawa et al., U.S. Pat. No. 4,340,598 discloses imidazol-5-yl-acetic acids and imidazol-5-yl-propanoic acids. Specifically, the discloser includes 1-benzyl-2-n-butyl-5-chloroimidazole-4-acetic acid and 1-benzyl-2-phenyl-5-chloroimidazole-4-propanoic acid.

Furukawa, et al., U.S. Pat. No. 4,355,040 discloses substituted imidazole-5-acetic acid derivatives. A compound specifically disclosed is 1-(2-chlorobenzyl)-2-n-butyl-4-chloroimidazole-5-acetic acid.

Carini et al. in EP 253,310 disclose certain imidazolyl-propenoic acids. Two intermediates described in this patent are ethyl 3-[1-(4-nitrobenzyl)-2-butyl-4-chloroimidazol-5-yl]propenoate and ethyl 3-[2-butyl-4-chloro-1-(4-aminobenzyl)imidazol-5-yl]propenoate.

Also, Wareing, in PCT/EP 86/00297, discloses as intermediates certain imidazolylpropenoate compounds. On page 62, Formula (CX) is ethyl 3-[1(-4-fluorophenyl)-4-isopropyl-2-phenyl-1H-imidazol-5-yl]-2-propenoate.

DESCRIPTION OF THE INVENTION

The compounds of the present invention that are blockers of angiotensin II receptors are represented by the following Formula (I):

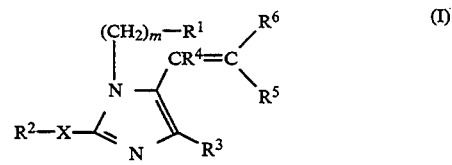

in which:

$R^1$ is Het, wherein Het is defined as a stable 5- to 7-membered monocyclic or 7- to 10-membered bicyclic heterocyclic ring, which is either saturated or unsaturated, and which consists of carbon atoms and from one to three heteroatoms selected from the group consisting of N, O, S, wherein the nitrogen and sulfur atoms may optionally be oxidized, and the nitrogen heteroatom may optionally be quarternized, and including any bicyclic group in which any of the above-defined heterocyclic rings is fused to a benzene ring and wherein the Het is unsubstituted or substituted by any accessible stable combination of up to three substituents selected from the group consisting of $C_1$–$C_6$alkyl, $C_1$–$C_6$alkoxy, Cl, Br, F, I $NR^7R^7$, A—$CO_2R^7$, $CONR^7R^7$, $SO_3H$, $SO_2NHR^7$, OH, $NO_2$, W, $SO_2C_1$–$_6$alkyl, $SO_2W$, $SC_1$–$C_6$alkyl, $NR^7COW$, or $NR^7COC_1$–$C_6$alkyl, wherein W is $C_nF_{2n+1}$, in which n is 1–3 and wherein A is —CH=CH—, —$(CH_2)_{0-4}$—, —Q—$CH(R^9)$—, or —Q—$(CH_2)_{1-2}$—U—$(CH_2)_{1-2}$—, in which Q is O, S, NH, or $NC_1$–$_6$alkyl, U is absent or present as O, S, NH, or $NC_1$–$_6$alkyl, and $R^9$ is hydrogen, phenyl, or benzyl; m is 0–4;

$R^2$ is $C_2$–$C_{10}$alkyl, $C_3$–$C_{10}$alkenyl, $C_3$–$C_{10}$alkenyl, $C_3$–$C_6$cycloalkyl, or $(CH_2)_{0-8}$phenyl unsubstituted or substituted by one to three substituents selected from $C_1$–$_6$alkyl, nitro, Cl, Br, F, I, hydroxy, $C_1$–$C_6$alkoxy, $NR^7R^7$, $CO_2R^7$, CN, $CONR^7R^7$, W, tetrazol-5-yl, $NR^7COC_1$-$C_6$alkyl, $NR^7COW$, $SC_1$-$C_6$alkyl, $SO_2W$, or $SO_2C_1$-$C_6$alkyl;

X is a single bond, S, $NR^7$, or O;

$R^3$ is hydrogen, Cl, Br, F, I, CHO, hydroxymethyl, $COOR^7$, $CONR^7R^7$, $NO_2$, W, CN, $NR^7R^7$, or phenyl;

$R^4$ and $R^5$ are independently hydrogen, $C_{1-6}$alkyl, phenyl-Y—, biphenyl-Y—, naphthyl-Y—, 2- or 3-thienyl-Y—, 2- or 3-furyl-Y—, 2-, 3- or 4-pyridyl-Y—, pyrazolyl-Y—, imidazolyl-Y—, pyrrolyl-Y—, triazolyl-Y—, oxazolyl-Y—, isoxazolyl-Y—, thiazolyl-Y—, or tetrazolyl-Y—, with each aryl or heteroaryl group being unsubstituted or substituted by $C_{1-6}$alkyl, $C_1$-$C_6$alkoxy, Cl, Br, F, I, $NR^7$, $R^7$, $CO_2R^7$, $SO_2NHR^7$, $SO_3H$ $CONR^7R^7$, OH, $NO_2$, W, $SO_2W$, $SC_1$-$C_6$alkyl, $SO_2C_1$-$C_6$alkyl, $NR^7COH$, $NR^7COW$, or $NR^7COC_1$-$C_6$alkyl;

Y is a single bond, O, S, or $C_1$-$C_6$alkyl which is straight or branched or optionally substituted by phenyl or benzyl, wherein each phenyl or benzyl group is unsubstituted or substituted by halo, $NO_2$, $CF_3$, $C_{1-6}$alkyl, $C_1$-$C_6$alkoxy, CN, or $CO_2R^7$;

$R^6$ is —Z—$COOR^8$, —Z—$CONR^7R^7$, or —Z—tetrazol-5-yl;

Z is a single bond, vinyl, —$CH_2$—O—$CH_2$—, methylene optionally substituted by $C_1$-$C_6$alkyl, one or two benzyl groups, thienylmethyl, or furylmethyl, or —C(O)$NHCHR^9$—, wherein $R^9$ is H, $C_1$-$C_6$alkyl, phenyl, benzyl, thienylmethyl, or furylmethyl;

W is $C_nF_{2n+1}$, wherein n is 1-3;

each $R^7$ independently is hydrogen, or $C_1$-$C_6$alkyl; and $R^8$ is hydrogen, $C_1$-$C_6$alkyl, or 2-di($C_1$-$C_6$alkyl)-amino-2-oxoethyl; or a pharmaceutically acceptable salt thereof.

Preferably, one of $R^4$ and $R^5$ is hydrogen or $C_1$-$C_6$alkyl.

Preferred $R^1$ Het groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, 2-, 3-, or 4- pyridyl, pyrazinyl, pyrimidinyl, pyridazinyl, oxazolyl, oxazolidinyl, isolazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoxazolyl, 2-, or 3- furyl, pyranyl, tetrahydrofuryl, tetrahydropyranyl, 2-, or 3-thienyl, benzothienyl, benzoxazolyl, thiamorpholinyl, thiamorpholinyl sulfoxide, thiamorpholinyl sulfone, benzofuranyl, and oxadiazolyl, wherein the $R^1$ group is unsubstituted or substituted by any accessible stable, combination of up to three substituents selected from the group consisting of $C_1$-$C_6$alkyl, $C_1$-$C_6$alkoxy, Cl , Br, F, I, $NR^7R^7$, A—$CO_2R^7$, $CONR^7R^7$, $SO_3H$, $SO_2NHR^7$, OH, $NO_2$, W, $SO_2C_1$-$C_6$alkyl, $SO_2W$, $SC_1$-$C_6$alkyl, $NR^7COW$, or $NR^7COC_1$-$C_6$alkyl, wherein W is $C_nF_{2n+1}$, in which n is 1-3 and wherein A is —CH=CH—, —$(CH_2)_{0-4}$—, —Q—CH($R^9$)—, or —Q—$(CH_2)_{1-2}$—U—$(CH_2)_{1-2}$—, in which Q is O, S, NH, or $NC_{1-6}$alkyl, U is absent or present as O, S, NH, or $NC_{1-6}$alkyl, and $R^9$ is hydrogen, phenyl, or benzyl.

The most preferred compounds of this invention are represented by Formula (I) when:

$R^1$ is 2- or 3-thienyl, 2- or 3-furyl, or 2-, 3-, or pyridyl with each thienyl, furyl, or pyridyl group being unsubstituted or substituted by $CO_2R^7$;

m is 0-2;

X is a single bond or S;

$R^2$ is $C_2$-$C_8$alkyl;

$R^3$ is hydrogen, chloro, fluoro, or trifluoromethyl;

$R^4$ is hydrogen or $C_1$-$C_6$alkyl;

$R^5$ is 2-, or 3-thienyl-Y—, 2-, or 3-furyl-Y—, or 2- or 3-, or 4-pyridyl-Y—, with each heteroaryl group being unsubstituted or substituted by methyl or methoxy;

Y is a single bond or $C_1$-$C_6$alkyl which is straight or branched;

$R^6$ is —Z—$COOR^8$;

Z is a single bond; and $R^8$ is hydrogen or $C_1$-$C_6$alkyl; or a pharmaceutically acceptable salt thereof.

The E isomers (trans stereochemistry of the $COOR^8$ and imidazole groups) are generally more active and thus, are preferred over the Z isomers (cis).

As used herein, the terms alkyl, alkenyl, alkoxy and alkenyl mean carbon chains which are branched or unbranched with the length of the chain determined by the descriptor preceding the term.

Particular compounds of the invention include, but are not limited to, the following:

(E)-3-[2-n-butyl-1-{(5-carboxy-2-thienyl)methyl}-1H-imidazol-5-yl]-2-(2-thienyl)methyl-2-propenoic acid, (E)-3-[2-n-butyl-1-{(5-carboxy-3-thienyl)methyl}-1H-imidazol-5-yl]-2-(2-thienyl)methyl-2-propenoic acid, (E)-3-[2-n-butyl-1-{(5-carboxy-2-furyl)methyl}-1H-imidazol-5-yl]-2-(2-thienyl)methyl-2-propenoic acid, and (E)-3-[2-n-butyl-1-{(5-carboxy-2-pyridyl)methyl}-1H-imidazol-5-yl]-2-(3-thienyl)methyl-2-propenoic acid;

or a pharmaceutically acceptable salt thereof.

The most preferred compound of this invention is (E)-3-[2-n-butyl-1-{(5-carboxy-2-thienyl)methyl)-1H-imidazol-5-yl]-2-(2-thienyl)methyl-2-propenoic acid or a pharmaceutically acceptable salt thereof.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of producing antihypertensive activity and methods of treating congestive heart failure, glaucoma, and renal failure by administering these compounds are also included in this invention.

The present invention also provides for the use of a compound of Formula (I) in the manufacture of a medicament for the treatment of diseases in which angiotensin II receptor antagonism is a factor, such as hypertension, congestive heart failure, glaucoma, and renal failure.

The compounds of this invention are prepared by procedures described herein and illustrated by the examples. Reagents, protecting groups and functionality on the imidazole and other fragments of the molecule must be consistent with the proposed chemical transformations. Steps in the synthesis must be compatible with the functional groups and the protecting groups on the imidazole and other parts of the molecule.

The starting materials, 2-$R^2$X-imidazole, are known to the art (J. Org. Chem. 45:4038, 1980) or are synthesized by known procedures. For example, imidazole is converted to 2-n-butylimidazole by reacting imidazole with triethylorthoformate and p-toluenesulfonic acid to give 1-diethoxyorthoamide imidazole and then treating with n-butyl lithium to give the 2-lithium derivative of the orthoamide and alkylating with n-butyl iodide in a suitable solvent, such as tetrahydrofuran (THF).

The following procedure is useful for the preparation of compounds of Formula (I) particularly where $R^1$ is 2-thienyl substituted by a carboxy, m is one, $R^2$ is n-butyl or n-propyl, X is a single bond or S, $R^3$ is hydrogen, chloro, or $CF_3$, $R^4$ is hydrogen, $R^5$ is 2-thienylmethyl, $R^6$ is $COOR^8$ and $R^8$ is hydrogen, methyl, or ethyl.

The 1-$R^1$ $(CH_2)_m$-group is incorporated onto the 2-$R^2$X-imidazole by known procedures, for example, by reaction with an $R^1$-$(CH_2)_m$-halide, mesylate or acetate, such as 5-bromomethyl-2-carbomethoxythiophene, in a suitable solvent, such as dimethylformamide (DMF), in the presence of a suitable acid acceptor, such as sodium alkylate, potassium or sodium carbonate, or a metal hydride, preferably sodium hydride, at a reaction temperature of about 25° C. to about 100° C., preferably at 50° C. The resulting 1-$R^1(CH_2)_m$-2-$R^2$X-imidazole is hydroxymethylated in the 5-position, for example, by reacting this compound with formaldehyde in the presence of sodium acetate acetic acid to provide the 1-$R^1CH_2$-2-$R^2$X-5-hydroxymethyl-imidazole intermediate. The hydroxymethyl group is oxidized to an aldehyde by treatment with a suitable reagent, such as anhydrous chromic acid-silica gel in tetrahydrofuran or, preferably, with activated manganese dioxide, in a suitable solvent, such as benzene or toluene, or preferably methylene chloride, at a temperature of about 25° C. to about 140° C., preferably at 25° C., to give 1-$R^1(CH_2)_m$-2-$R^2$X-imidazol-5-carboxaldehydes.

Alternatively, the 1-$R^1(CH_2)_m$-2-$R^2$-imidazol-5-carboxaldehydes are prepared by the following procedure. An imido ether, $R^2$—C(=NH)—O—alkyl, such as valeramidine methyl ether, is reacted with dihydroxyacetone in liquid ammonia under pressure to give 2-$R^2$-5-hydroxymethyl-imidazole. The hydroxymethyl group is oxidized to the corresponding aldehyde as hereinbefore described, for example, using manganese dioxide in a suitable solvent, such as methylene chloride. The 2-$R^2$-imidazol-5-carboxaldehydes are reacted with an N-alkylating protecting reagent, such as chloromethyl pivalate (POMCl), in the presence of a base, such as potassium carbonate, in a suitable solvent, such as dimethylformamide, at a temperature of about 20° C. to about 50° C. preferably at 25° C., to give N-alkylation (e.g., POM-derivation) on the least hindered nitrogen atom of the imidazole nucleus. The 1-$R^1(CH_2)_m$-group is incorporated onto the imidazole by N-alkylation of the above prepared aldehyde with, for example, a halomethylheteroaryl compound, such as 5-bromomethyl-2carbomethoxythiophene, at a temperature of about 80° C. to about 125° C., preferably at 100° C. The protecting group on the 3-nitrogen of the imidazole ring is removed by base hydrolysis, for example using a biphasic mixture of ethyl acetate and aqueous sodium carbonate, to give 1-$R^1(CH_2)_m$-2-$R^2$-imidazole-5-carboxaldehydes compounds.

Alternately, the 1-$R^1(CH_2)_m$-2-$R^2$-imidazol-5-carboxaldehydes are prepared form the 2-$R^2$-5-hydroxymethylimidazoles using the following procedure. The 5-hydroxymethyl intermediate is halogenated in the 4-position, for example using N-chlorosuccinimide, in a suitable solvent, such as tetrahydrofuran in 2-methoxyethane, at a temperature of about 25° C. to about 60° C., preferably at 50° C. The 5-hydroxymethyl group of this intermediate is oxidized to the 5-carboxyaldehyde using the methods hereinbefore described. The resulting imidazole intermediate is selectively N-alkylated in the 1-position using, for example, a halomethylheteroaryl compound, such as 5-bromomethyl-2-carbomethoxythiophene, in the presence of a base, such as potassium carbonate, in a suitable solvent, such a dimethylformamide. The halo group is removed by hydrogenolysis in the presence of a catalyst, such as palladium on carbon, to give 1-$R^1(CH_2)_m$-2-$R^2$-5-hydroxymethylimidazoles. The 1-$R^1(CH_2)_m$-2-$R^2$-imidazol-5-carboxaldehydes are prepared from the 5-hydroxymethyl compounds by the method described previously.

Formula (I) compounds are prepared from the 1$R^1(CH_2)_m$-2-$R^2$X-imidazol-5-carboxyaldehydes in a reaction with an appropriately substituted phosphonate, such as trimethyl 3-(2-thienyl)-2-phosphonopropionate. The phosphonates are prepared from appropriate trialkyl phosphonoacetates by alkylation with an appropriate halide, mesylate or acetate in the presence of a suitable base, such as sodium hydride, in a suitable solvent, preferably glyme at a reaction temperature of 25° C. to 110° C., preferably at 55° C., to provide, for example, the phosphonates. The reaction of the imidazol-5-carboxaldehydes with the phosphonates is performed in the presence of a suitable base, such as a metal alkoxide, lithium hydride or preferably sodium hydride, in a suitable solvent, such as ethanol, methanol, ether, dioxane, tetrahydrofuran, or preferably glyme, at a reaction temperature of about 10° C. to about 50° C., preferably at 25° C., to provide a variable mixture of trans and cis, e.g., (E) and (Z), 1-$R^1(CH_2)_m$-2-$R^2$X-5-CH=C($R^5$)(COOalkyl)-imidazoles. These isomers are separated by chromatography over silica gel in suitable solvent systems, preferably hexane in ethyl acetate. The esters are hydrolyzed to the acids, 1-$R^1$—$(CH_2)_m$-2-$R^2$X-5-CH=C($R^5$)COOH—imidazoles, using base, such as potassium hydroxide, lithium hydroxide or sodium hydroxide, in a suitable solvent system, such as, for example, aqueous alcohols or diglyme. The trans and cis structures of the acids are readily determined by NMR by the NOE protocol, as well as by the biological activities since, generally, the trans (E) isomeric acids are the more potent isomers.

Formula (I) compounds also are prepared by the following procedure. The 2-$R^2$X-imidazole starting materials are reacted with trimethylsilylethoxymethyl (SEM) chloride to give 1-(trimethylsilyl)ethoxy-methyl- 2-$R^2$X-imidazole. The reaction is carried out, for example, in the presence of sodium hydride in a solvent such as dimethylformamide. The 5-tributyltin derivatives are prepared by lithiation with, for example, butyllithium in a suitable solvent, preferably diethyl ether, followed by treatment of the lithio imidazole derivative with a tributyltin halide, preferably tri-N-butyltin chloride, at about −10° C. to about 35° C., preferably at 25° C. The 1-SEM-2-$R^2$X-5-tributyltin-imidazole is coupled with an α,β-unsaturated acid ester having a leaving group on the β-position, such as a halide or trifluoromethanesulfonyloxy group, for example, BrC$R^4$=C($R^5$)(COOalkyl), in the presence of a phosphine ligand, such as bis (diphenylphosphino)propane, or triphenylphosphine and a palladium (II) compound, or preferably tetrakis (triphenylphosphine) palladium (O), with or without a base, such as tributylamine, at a temperature of about 50° C. to about 150° C., preferably at 120° C.

Both the (E) and (Z) olefinic isomers are prepared by this procedure, and the isomeric esters are separated by chromatography over silica gel. The 1-SEM group from the (E) and (Z) isomers is hydrolyzed with acid, for example, aqueous hydrochloric, in a suitable alcoholic solvent, such as methanol or ethanol, and the 1-unsubstituted imidazole derivatives are converted to the 1-t-butoxycarbonyl (t-BOC) imidazoles with di-t-butyl dicarbonate (Hoppe-Seyler's Z. Physiol. Chem., (1976), 357, 1651). The t-BOC esters are alkylated and hydrolyzed with, for example, 2-thienylmethyl-O-triflate, in the presence of a suitable base, preferably diisopropylethylamine, in a suitable solvent, preferably methylene chloride, to afford the 1-(heteroaryl)methylimidazole derivatives (esters). The (E) and (Z) isomers are hydrolyzed to the (E) and (Z) acids by the method described above.

Compounds of Formula (I) are also prepared by the following procedure. The $1\text{-}R^1(CH_2)_m\text{-}2\text{-}R^2X$-imidazole-5-carboxaldehydes, prepared as described above, are reacted with a substituted half-acid, half-ester derivative of a malonate, such as ethyl 2-carboxy-3-(2-thienyl)propionate, in the presence of a base, such as piperidine, in a suitable solvent, such as toluene or benzene, at a temperature of about 80° C. to about 110° C., preferably at 80° C. The resulting $1\text{-}R^1(CH_2)_m\text{-}2\text{-}R^2X\text{-}5\text{-}CH=C(R^5)COO$alkyl-imidazoles are hydrolyzed to the corresponding Formula (I) acid compounds by alkaline hydrolysis as described above.

Compounds of Formula (I) also are prepared as follows. The $1\text{-}R^1(CH_2)m\text{-}2\text{-}R^2X$-imidazol-5-carboxaldehydes, prepared as described above, are converted to the corresponding alcohols with an organometallic derivative or Grignard reagent, preferably methyl lithium, in a suitable solvent, such as tetrahydrofuran. The alcohol is oxidized, for example, using manganese dioxide to give the ketone. The olefinic esters are prepared from the ketone by reaction with appropriate phosphonates to give the (E) and/or (Z) isomers which are readily separated. The acids are prepared from the esters by alkaline hydrolysis as described above.

Additionally, compounds of Formula (I) are prepared as follows. The $1\text{-}R^1\text{-}(CH_2)_m\text{-}2\text{-}R^2X$-imidazol-5-carboxaldehydes are treated with the lithium derivative of a substituted ethyl or methyl ester. These lithio derivatives are prepared from the reaction of lithium diisopropylamide in a suitable solvent, preferably tetrahydrofuran, with an acid ester, such as $ROOC\text{—}CH_2\text{—}Y\text{—}(2\text{-thienyl})$, to generate the α-lithio derivatives at about −78° C. to about −10° C., preferably at −78° C., which are then treated with the imidazol-carboxaldehyde. The intermediate β-hydroxy group of the imidazole ester is converted to a mesylate or an acetate and the mesylate, or preferably the acetate, is heated in a suitable solvent, such as toluene, with one to two equivalents of 1,8-diazo-bicyclo[5.4.0]undec-7-ene, at about 50° C. to about 110° C., preferably at 80° C., to afford ester compounds of Formula (I), such as 3-(imidazol-5-yl)-2-(2-thienyl)methyl-2-propenoic acid esters. The (E) isomer is the predominate olefinic isomer. The acids are prepared from the esters by the method described above.

Compounds of Formula (I) wherein Y is a single bond, $R^5$ is an aryl or heteroaryl as described in Formula (I) and $R^6$ is COOH may be prepared by heating $1\text{-}R^1\text{—}(CH_2)_m\text{-}2\text{-}R^2X$-imidazol-5-carboxaldehydes at about 50° C. to about 180° C., preferably at 140° C., with an appropriately substituted acetic acid, acetic anhydride, and potassium carbonate to provide unsaturated acids of Formula (I), such as 3-[2-n-butyl-1-(2-thienyl)methyl-1H-imidazol-5-yl]-2-$R^5$-2-propenoic acid. The trans olefinic acid is the principal product.

Compounds of Formula (I) in which $R^6$ is Z—COOR$^8$ where Z is an optionally substituted methylene group are prepared by reducing the trans or (E) isomers of 3-(imidazol-5-yl)-2-propenoic acid esters (prepared as described above) with an appropriate hydride reagent, preferably diisobutylaluminum hydride, in a suitable solvent, such as tetrahydrofuran, to provide the unsaturated alcohol compounds. These compounds are reacted with ethyl chloroformate, for example, with a base, preferably triethylamine, in a suitable solvent, such as tetrahydrofuran, to give 5-$EtOOCOCH_2CR^5=CR^4$-imidazoles which are reacted with carbon monoxide in the presence of a phosphine ligand, preferably triphenylphosphine with palladium (II) acetate, in a suitable solvent, preferably tetrahydrofuran, at a temperature of about 25° C. to about 100° C., preferably at 40° C., to give the 5-$EtOOCCH_2CR^5=CR^4$-imidazoles. The corresponding acids are prepared from these ethyl esters by base hydrolysis as described above.

Compounds of Formula (I) in which Z is —CH$_2$COOR$^8$ having additional substitution on the carbon a to the carboxylate group are prepared by converting 5-$EtOOCH_2CR^5=CH_4$-imidazoles to the lithium derivative of the ester with a lithium dialkylamide, preferably lithium diisopropylamide, and then treating with an alkylating agent, such as methyl halide, benzyl bromide, or heterocyclic methyl halide, to provide the monoalkylated product compounds or the dialkylated product compounds. The acid compounds are prepared from the esters by base hydrolysis.

Compounds of Formula (I) in which $R^6$ is Z—COOR$^8$ where Z is —CH$_2$—O—CH$_2$— are prepared from unsaturated alcohol compounds, which had been obtained by the reduction of the Formula (I) propenoic acid esters. The alcohol is reacted with an appropriate hydride reagent, such as sodium hydride, in a suitable solvent, such as glyme, followed by reaction with an alkylating reagent, such as methyl bromoacetate, to give the 5-$MeOOCCH_2$—O—$CH_2CR^5=CR^4$-imidazoles. The corresponding acids are prepared from these esters by base hydrolysis as described above.

Compounds of Formula (I) in which $R^6$ is Z—COOR$^8$ where Z is —C(O)NHCHR$^9$— are prepared from the Formula (I) propenoic acid compounds. These acids are reacted with an appropriately substituted amino acid, such as glycine methyl ester hydrochloride or phenylalanine methyl ester hydrochloride, in the presence of an amide-forming reagent, such as N-hydroxysuccinimide and dicyclohexylcarbodiimide, in the presence of a base, for example triethylamine, in a suitable solvent, such as tetrahydrofuran, at a temperature of about 20° C. to about 50° C., preferably at 35° C. The 5-$C_{1-4}$alkylOOCCHR$^9$NHC(O)—$CH_2CR^5=CR^4$-imidazoles are converted to their corresponding acids by base hydrolysis as described above.

compounds of Formula (I) in which $R^6$ is Z-tetrazol-5-yl are prepared from the corresponding Z—COOH compounds. For example, Formula (I) acid compounds are reacted with a halogenating agent, such as thionyl chloride, in a suitable solvent, for example benzene, to give the corresponding acid halide compounds. The acid halides are then converted to primary amide compounds in a reaction with concentrated ammonia. Subsequent dehydration of the amides with oxalyl chloride/dimethylformamide in acetonitrile/dimethylformamide yields the nitrile compounds, which are the immediate precursors to the Formula (I) tetrazole compounds. Tetrazole formation is accomplished by reacting the nitriles with azide, preferably aluminum azide prepared in situ by the reaction of sodium azide with aluminum chloride, in a suitable solvent, for example tetrahydrofuran.

Compounds of Formula (I) in which the $R^1$ substituent is substituted by hydroxy are prepared from Formula (I) compounds in which the $R^1$ group is substituted by $C_1$-$C_4$alkoxy using an ether-cleaving reagent, such as boron tribromide or hydrobromic acid.

Compounds of Formula (I) in which the $R^1$ substituent is substituted by carboxy are prepared from Formula (I) compounds in which the $R^1$ group is substituted by $CO_2C_1$-$C_4$alkyl using basic hydrolysis, such as aqueous sodium or potassium hydroxide in methanol or ethanol, or using acidic hydrolysis, such as aqueous hydrochloric acid.

Compounds of Formula (I) in which the $R^1$ substituent is substituted by $CONR^7R^7$ are prepared from Formula (I) compounds in which the $R^1$ group is substituted by carboxy. The carboxy compounds are reacted with a halogenating agent, such as thionyl chloride, followed by reaction with an appropriately substituted amine, $NR^7R^7$, wherein $R^7$ is as defined for Formula (I) compounds.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Pharmaceutically acceptable base addition salts of compounds of Formula (I) in which $R^8$ is H are prepared by known methods from organic and inorganic bases, including nontoxic alkali metal and alkaline earth bases, for example, calcium, lithium, sodium, and potassium hydroxide; ammonium hydroxide, and nontoxic organic bases, such as triethylamine, butylamine, piperazine, meglumine, choline, diethanolamine, and tromethamine.

Angiotensin II antagonist activity of the compounds of Formula (I) is assessed by in vitro and in vivo methods. In vitro antagonist activity is determined by the ability of the compounds to compete with 125I-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.
Binding The radioligand binding assay is a modification of a method previously described in detail (Gunther et al., Circ. Res. 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the $IC_{50}$ which is the concentration of antagonist needed to displace 50% of the total specifically bound angiotensin II. Exemplary of the IC50 of compounds of the invention (E isomers) is, about 1.0 nM to about 10 μM.

Aorta

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist disassociation constants ($K_B$) are calculated by the dose ratio method using the mean effective concentrations. Exemplary of the $K_B$ of compounds of the invention (E isomers) is about 0.1 nM to about 20 μM.

Inhibition of pressor response to angiotensin II in conscious rats

Rats are prepared with indwelling femoral arterial and venous catheters and a stomach tube (Gellai et al., Kidney Int. 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 0.1 to 300 mg/kg. The dose of compound needed to produce 50% inhibition of the control response to angiotensin II ($IC_{50}$) is used to estimate the potency of the compounds.

Antihypertensive activity

The antihypertensive activity of the compounds is measured by their ability to reduce mean arterial pressure in conscious rats made renin-dependent hypertensive by ligation of the left renal artery (Cangiano et al., J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally. The dose of compound needed to reduce mean arterial pressure by 30 mm Hg ($IC_{30}$) is used as an estimate of potency.

The intraocular pressure lowering effects employed in this invention may be measured by the procedure described by Watkins, et al., J. Ocular Pharmacol., 1 (2):161–168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per, dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmolgic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components, such as quarternary ammonium compounds; buffering ingredients, such as alkali metal chloride; antioxidants, such as sodium metabisulfite; and other conventional ingredients, such as sorbitan monolaurate.

Additionally, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, nontoxic quantity selected from the range of 0.01–200 mg/kg of active compound, preferably 1–100 mg/kg. The selected dose is administered to a human patient in need of angiotensin II receptor antagonism from 1–6 times daily, orally, rectally, topically, by injection, or continuously by infusion. Oral dosage units for human administration preferably contain from 1 to 500 mg of active compound. Preferably, lower dosages are used for parenteral administration. Oral administration, at higher dosages, however, also can be used when safe and convenient for the patient. Topical formulations contain the active compound in an amount selected from 0.0001 to 0.1 (w/v %), preferably from 0.0001 to 0.01. As a topical dosage unit form, an amount of active compound from between 50 ng to 0.05 mg, preferably 50 ng to 5 $\mu$g, is applied to the human eye.

The method of this invention of antagonizing angiotensin II receptors in mammals, including humans, comprises administering to a subject in need of such antagonism an effective amount of a compound of Formula (I). The method of this invention of producing antihypertensive activity and the method of treating congestive heart failure, glaucoma, and renal failure comprise administering a compound of Formula (I) to a subject in need thereof an effective amount to produce said activity.

Contemplated equivalents of Formula (I) compounds are compounds otherwise corresponding thereto wherein substituents have been added to any of the unsubstituted positions of the Formula (I) compounds provided such compounds have the pharmaceutical utility of Formula (I) compounds.

The following examples illustrate preparation of compounds and pharmaceutical compositions of this invention. The examples are not intended to limit the scope of this invention as defined hereinabove and as claimed below.

EXAMPLE 1

(E)-3-[2-n-Butyl-1-{(5-carboxy-2-thienyl)methyl}-1H-imidazol-5-yl]-2-(2-thienyl)methyl-2-propenoic Acid (i) 2-n-butyl-1-pivalyloxymethylimidazol-5-carboxaldehyde A mixture of valeramidine methylether hydrochloride (250 g, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3L). The resulting slurry was refluxed with acetonitrile (1L). The solution was decanted from the solid ammonium chloride while hot. This procedure was repeated, and the combined acetonitrile extracts were treated with charcoal, filtered hot and the filtrate was concentrated in vacuo to give the dark oil, 2-n-butyl-5-hydroxymethylimidazole (235 g, 1.63.mol, 98%).

The 5-hydroxymethylimidazole (16.92 g, 0.111 mol) was dissolved in one liter of methylene chloride. To this solution was added 45 grams of manganese dioxide. After stirring at room temperature for four hours, the solids were filtered off and the solvent was removed in vacuo. The crude 2-n-butyl-imidazol-5-carboxaldehyde was used without further purification (16.9 g).

A suspension of 2-butylimidazol-5-aldehyde (16.9 g, 0.111 mol), chloromethyl pivalate (21.77 g, 0.145 mol), and potassium carbonate (20.07 g, 0.145) in 200 ml of dimethylformamide was stirred at ambient temperature under argon for four days. The solids were removed by filteration and washed with ether. The combined filtrates were partitioned between diethyl ether and water. The ether phase was washed successively with water and brine, dried over magnesium sulfate and concentrated under vaccum to give 23.6 g of 2-n-butyl-1-pivalyloxymethylimidazol-5-carboxaldehyde.

(ii) 5-bromomethyl-2-carbomethoxythiophene

A solution of 5-methyl-2-thiophene carboxylic acid (25 g, 0.176 mol) in 500 ml of methanol was saturated with gaseous hydrochloric acid at 0° C. The reaction mixture was stirred at room temperature for 18 hours and then refluxed for 48 hours. The solvent was removed in vacuo and the crude methyl 5-methyl-2-thiophene carboxylate was used without further purification.

The methyl ester prepared above (11.07 g, 0.071 mol) was dissolved in 200 ml of carbon tetrachloride under argon. N-bromosuccinimide (13.25 g, 0.074 mol) and dibenzoyl peroxide were then added. The reaction mixture was refluxed for 2 hours and allowed to stand at room temperature for 18 hours. The solids were collected and the filtrate was concentrated in vacuo to give 19 g of 5-bromomethyl-2-carbomethoxythiophene.

(iii) 2-n-butyl-1-[(5-carbomethoxy-2-thienyl)methyl]imidazol-5-carboxaldehyde

A mixture of 2-n-butyl-1-pivalyloxymethylimidazol-5-carboxaldehyde (5.0 g, 0.019 mol) and 5-bromomethyl-2-carbomethoxy thiophene (4.86 g, 0.021 mol) was heated to 100° C. under argon for 18 hours. Repeated trituration with ether gave 9.4 g of a crystalline salt. A suspension of this salt in 150 ml of ethyl acetate was stirred for 0.5 hours with 150 ml of 5% aqueous sodium carbonate. The layers were separated, the aqueous layer washed with ethyl acetate, and the combined organic layers washed with water, dried over magnesium sulfate and concentrated to give an oil. Chromatography of this oil over silica gel eluting with ethyl acetate/hexane (1:1) gave 0.62 g of 2-n-butyl-1-[(5-carbomethoxy-2-thienyl)methyl]imidazol-5-carboxaldehyde.

(iv) ethyl 2-carboxy-3-(2-thienyl)propionate

The title compound was prepared by stirring a solution of diethyl 2-thienylmalonate (16.8 g, 0.0655 mol) and potassium hydroxide (4.41 g, 0.0786 mol) in 200 ml of ethanol under argon at room temperature for 12 days and then purifying by removing the solvent under vacuum, dissolving the residue in water, washing the aqueous layer with aqueous hydrochloric acid and extracting the product with diethyl ether. The solvent was removed in vacuo to give 14 g of theyl 2-carboxy-3-(2-thienyl)propionate.

(v) ethyl (E)-3-[2-n-butyl-1-{(5-carbomethoxy-2-thienyl)methyl}-1H-imidazol-5-yl]-2-(2-thienyl)methyl-2-propenoate A mixture of 2-n-butyl-1-[(5-carbomethoxy-2-thienyl)methyl]imidazol-5-carboxaldehyde (0.5 g, 1.66 mmol), ethyl 2-carboxy-3-(2-thienyl)propionate (1.14 g, 4.99 mmol), piperidine (0.155 g, 1.83 mmol), 0.5 ml of pyridine in 50 ml of benzene were refluxed for 18 hours under argon in the presence of a Dean-Stark trap. The crude product was flash chromatographed over silica gel eluting with ethyl acetate/hexane (1:1) to give 0.474 g (49%) of ethyl (E)-3-[2-n-butyl-1-{(5-carbomethoxy-2-thienyl)methyl}-1H-imidazol-5-yl]-2-(2-thienyl)methyl-2propenoate.

(vi) (E)-3-[2-n-butyl-1-{(5-carboxy-2-thienyl)methyl}-1H-imidazol-5-yl]-2-(2-thienyl)methyl-2-propenoic acid A solution of ethyl (E)-3-[2in-butyl-1-{(5-carboxy-2-thienyl)methyl}-1H-imidazol-5-yl]-2-(2-thienyl)methyl-2-propenoate (474 mg, 1.0 mmol) in ethanol (10 ml) was treated with 10% potassium hydroxide solution (5 ml) and the solution was stirred for 18 hours at 25° C. The ethanol was removed in vacuo and the reaction mixture was partitioned between water and diethyl ether. The aqueous layer was washed with diethyl ether (3 X) and then the pH was adjusted to 4.5 with aqueous hydrochloric acid solution. The solid was collected to provide 0.35 g of crude product. Crystallization from methanol gave 0.31 g (72%) of (E)-3-[2-n-butyl-1-{(5-carboxy-2-thienyl)methyl}-1H-imidazol-5-yl]-2-(2-thienyl)methyl-2-propenoic acid; mp 239°-240° C. (d).

EXAMPLE 2

(E)-3-[2-n-Butyl-1-{(5-carboxy-2-pyridyl)methyl}-1H-imidazol-5-yl]-2-(2-thienyl)]methyl-2-propenoic Acid (i) 2-n-butyl-4-chloro-5-hydroxymethylimidazole To a solution of 2-n-butyl-5-hydroxymethylimidazole (25 g, 0.162 mol, prepared in Example 1 (i)) in 250 ml of tetrahydrofuran and 250 ml of 2-methoxyethane under argon was added portionwise N-chlorosuccinimide (26 g, 0.195 mol). The reaction mixture was heated at 50°-55° C. for 2 hours. The solvents were removed in vacuo and the residue for 48 hours. The solid was filtered and then stirred with 100 ml of diethyl ether for 1 hour. The solid was collected to give 16 g (52%) of 2-n-butyl-4-chloro-5-hydroxymethylimidazole.

(ii) 2-n-butyl-1-[(5-carbomethoxy-2-pyridyl)methyl]-4-chloroimidazol-5-carboxaldehyde To a solution of 2-n-butyl-4-chloroimidazol-5-carboxaldehyde (17.9 g, 9.6 mmol, prepared from 2-n-butyl-4-chloro-5-hydroxymethylimidazole by manganese dioxide oxidation) in 24 ml of dimethylformamide under argon was added potassium carbonate (1.59 g, 11.5 mmol). After stirring at room temperature for 10 minutes, 2-bromomethyl-5-carbomethoxypyridine (2.32 g, 10 mmol, prepared form 6-methylnicotinic acid using the procedure of Example 1 (ii)) was added. The reaction mixture was stirred at 70° C. for 1.5 hours and then at room temperature for 18 hours. The reaction was partitioned between water and ethyl acetate. The layers were separated and the organic extract was washed with water and brine and dried with magnesium sulfate. The solvent was removed in vacuo and the crude product was flash chromatographed on silica gel eluting with 30% ethyl acetate in hexane to give 2.14 g (67%) of 2-n-butyl-1-[(5-carbomethoxy-2-pyridyl)methyl-4-chloroimidazol-5-carboxaldehyde.

(iii) 2-n-butyl-1-[(5-carbomethoxy-2-pyridyl)methyl]imidazol-5-carboxaldehyde

A mixture of 2-n-butyl-1-[(5-carbomethoxy-2-pyridyl)methyl-4-chloroimidazol-5-carboxaldehyde (1.6 g, 4.76 mmol), potassium acetate (0.47 g, 4.76 mmol), and 10% palladium on carbon (0.16 g) in 150 ml of methanol was hydrogenated at 28 psi for 2 hours. The solids were filtered and the filtrate was concnetrated in vacuo. The residue was dissolved in ethyl acetate and washed with 5% aqueous sodium carbonate solution and brine. The organic extract was dried with magnesium sulfate and concentrated in vacuo. The crude product (1.2 g) in 200 ml of methylene chloride was stirred with 3.0 g of manganese dioxide for 4 hours at room temperature. The solids were filtered off and the filtrate was concentrated to give 1.2 g of 2-n-butyl-1-[(5-carbomethoxy-2-pyridyl)methyl]imidazol-5-carboxaldehyde (iv) methyl 3-[2-n-butyl-1-{(5-carbomethoxy-2-pyridyl)methyl}-1H-imidazol-5-yl]-3-hydroxy-2-(2-thienyl)methylpropanoate To a solution of diisopropylamine (0.53 g, 4.98 mmol) in dry tetrahydrofuran (20 ml) held at −78° C. under argon was added n-butyl lithium (1.91 ml, 4.78 mol of 2.5M in toluene). After stirring the reaction mixture for 30 minutes, methyl 3-(2-thienyl)propanoate (0.746 g, 4.38 mol) in tetrahydrofuran (5 ml) was added. The mixture was stirred for 30 minutes at −78° C. A solution of 2-n-butyl-1-[(5-carbomethoxy-2-pyridyl)methyl-1H-imidazol-5-carboxaldehyde (1.2 g, 3.98 mmol) in tetrahydrofuran (5 ml) was added and the resulting mixture was stirred at −78° C. for 20 minutes. The reaction was partitioned between saturated ammonium chloride solution and diethyl ether, the organic extract was washed with brine, dried over anhydrous magnesium sulfate and concentrated to 1.8 g of methyl 3-[2-n-butyl-1 -{(5-carbomethoxy-2 -pyridyl)methyl-1H-imidazol-5-yl]-3-hydroxy-2-(2-thienyl)methylpropanoate.

(v) methyl 3-acetoxy-3-[2-n-butyl-1-{(5-carbomethoy-2-pyridyl)methyl}-1H-imidazol-5-yl]-2-(2-thienyl)methylpropanoate A solution of methyl 3-[2-n-butyl-1-{(5-carbomethoxy-2-pyridyl)methyl}-1H-imidazol-5-yl]-3-hydroxy-2-(2-thienyl)methylpropanoate (1.8 g, 3.98 mmol) in methylene chloride (10 ml) was treated with 4-dimethylaminopyridine (0.194 g, 1.59 mmol). Then acetic anhydride (0.49 g, 4.78 mmol) was added dropwise to the stirred mixture. The mixture was stirred for 18 hours, water (25 mL) was added, the mixture was stirred for 1 hour and then diluted with diethyl ether and saturated sodium bicarbonate solution. The ether layer was washed with brine, dried with anhydrous magnesium sulfate and evaporated to give 1.99 g of methyl 3-acetoxy-3-[2-n-butyl-1-{(5-carbomethoy-2-pyridyl)methyl}-1H-imidazol-5-yl]-2-(2-thienyl)methylpropanoate.

(vi) methyl (E)-3-[2-n-butyl-1-{(5-carbomethoxy-2-pyridyl)methyl}-1H-imidazol-5-yl]-(2-thienyl)methyl-2-propenoate A mixture of methyl 3-acetoxy-3-[2-n-butyl-1-{(5-carbomethoxy-2-thienyl)methyl}-1H-imidazol-5-yl]-2-(2-thienyl)methylpropanoate (1.99 g, 3.88 mmol) in dry toluene (150 ml) was treated with 17 ml of 1,8-diazabicyclo-[ 5.4.0]undec-7-ene (DBU) and the resulting solution was heated at 80° C. under argon for 1 hour. The solvent was evaporated, the residue triturated with diethyl ether and activated charcoal was added. After filtration, the filtrate was concentrated to give 6.29 g of an oil that was chromatographed over silica gel with hexane/ethyl acetate (1:1) to give 0.43 g (24%) of methyl (E)-3-[2-n-butyl-1-{(5-carbomethoxy-2-thienyl)methyl)-1H-imidazol-5-yl-2-(2-thienyl)methyl-2-propenoate.

(vii) (E)-3-[2-n-butyl-1-{(5-carboxy-2-pyridyl)methyl}-1H-imidazol-5-yl]-2-(2-thienyl)methyl-2-propenoic acid Basic hydrolysis of the above prepared ester (0.43 g, 0.95 mmol) according to Example 1 (vi) gave 0.278 g (70%) of (E)-3-[2-n-butyl-1-[(5-carboxy-2-pyridyl)-methyl]-1H-imidazol-5-yl]-2-(2-thienyl)methyl-2-propenoic acid; mp 212°–213° C.

EXAMPLE 3

(E)-3-[2-n-Butyl-1-{(5-carboxy-3-thienyl)methyl}-1H-imidazol-5-yl]-2-(2-thienyl)methyl-2-propenoic Acid The title compound was prepared following the procedures described in Example 1 (v–vi) using 2-n-butyl-1-[(5-carbomethoxy-3-thienyl)methyl]imidazol-5-carboxaldehyde (prepared by the methods described in Example 2 (i–iii)) in place of 2-n-butyl-1-[(5-carbomethoxy-2-thienyl)methyl]-imidazol-5-carboxaldehyde; mp 133°–135° C. (d).

EXAMPLE 4

(E)-3-[2-n-Butyl-1-{(5-carboxy-2-furyl)methyl}-1H-imidazol-5-yl]-2-(2-thienyl)methyl-2-propenoic Acid The title compound was prepared following the procedures described in Example 1 (v–vi) using 2-n-butyl-1-[(5-carbomethoxy-2-furyl)methyl]imidazol-5-carboxaldehyde (prepared by the method described in Example 2 (i–iii)) in place of 2-n-butyl-1-[(5-carbomethoxy-2-thienyl)methyl]-imidazol-5-carboxaldehyde; mp 115° C. (d).

EXAMPLE 5

An oral dosage form for administering orally active Formula (I) compounds is produced by screening, mixing and filling into hard gelatin capsules the ingredients in proportions, for example, as shown below.

| Ingredients | Amounts |
| --- | --- |
| (E)-3-[2-n-butyl-1-{(5-carboxy-2-thienyl)methyl}-1H-imidazol-5-yl]-2-(2-thienyl)methyl-2-propenoic acid | 100 mg |
| magnesium stearate | 10 mg |
| lactose | 100 mg |

EXAMPLE 6

The sucrose calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
| --- | --- |
| (E)-3-[2-n-butyl-1-{(5-carboxy-3-thienyl)methyl}-1H-imidazol-5-yl]-2-(2-thienyl)methyl-2-propenoic acid | 75 mg |
| calcium sulfate dehydrate | 100 mg |
| sucrose | 15 mg |
| starch | 8 mg |
| talc | 4 mg |
| stearic acid | 2 mg |

EXAMPLE 7

(E)-3-[2-n-Butyl-1-{(5-carboxy-2-thienyl)methyl}-1H-imidazol-5-yl]-2-(2-thienyl)methyl-2-propenoic acid, 50 mg, is dispersed in 25 ml of normal saline to prepare an injectable preparation.

EXAMPLE 8

A topical opthamological solution for administering Formula (I) compounds is produced by mixing under sterile conditions the ingredients in proportions, for example, as shown below.

| Ingredients | Amounts (mg/mL) |
| --- | --- |
| (E)-3-[2-n-butyl-1-{(5-carboxy-2-furo)methyl}-1H-imidazol-5-yl]-2-(2-thienyl)methyl-2-propenoic acid | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s.ad 1.0 mL |
| 1.0 N sodium hydroxide | q.s.ad pH 7.4 |

It is to be understood that the invention is not limited to the embodiments illustrated hereabove and the right to the illustrated embodiments and all modifications coming within the scope of the following claims is reserved.

What is claimed is:

1. A compound of the formula:

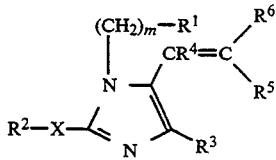

in which:
- $R^1$ is 2- or 3-thienyl, 2- or 3-furyl, or 2-, 3-, or 4-pyridyl, with each thienyl, furyl, or pyridyl being unsubstituted or substituted by $CO_2R^7$;
- m is 0–2;
- $R^2$ is $C_2$–$C_8$alkyl;
- X is a single bond or S;
- $R^3$ is hydrogen, chloro, fluoro, or trifluoromethyl;
- $R^4$ is hydrogen or $C_1$–$C_6$alkyl;
- $R^5$ is 2- or 3-thienyl-Y—, 2- or 3-furyl-Y—, or 2-, 3-, or 4-pyridyl-Y—, with each thienyl, furyl, or pyridyl being unsubstituted or substituted by methyl or methoxy;
- Y is a single bond or $C_1$–$C_6$alkyl, which is straight or branched;
- $R^6$ is —Z—$COOR^8$;
- Z is a single bond;
- $R^7$ is hydrogen or $C_1$–$C_6$alkyl;
- $R^8$ is hydrogen or $C_1$–$C_6$alkyl;

or a pharmaceutically acceptable salt thereof.

2. A compound of claim 1 which is the E isomer, wherein the $COOR^8$ group and the imidazole are trans to each other.

3. A compound of claim 2 which is (E)-3-[2-n-butyl-1-{(5-carboxy-2-thienyl)methyl}-1H-imidazol-5-yl]-2-(2-thienyl)methyl-2-propenoic acid or a pharmaceutically acceptable salt thereof.

4. A compound of claim 2 which is:
(E)-3-[2-n-butyl-1-{(5-carboxy-3-thienyl)methyl}-1H-imidazol-5-yl]-2-(2-thienyl)methyl-2-propenoic acid;
(E)-3-[2-n-butyl-1-{(5-carboxy-2-furyl)methyl}-1H-imidazol-5-yl]-2-(2-thienyl)methyl-2-propenoic acid; or
(E)-3-[2-n-butyl-1-{(5-carboxy-2-pyridyl)methyl}-1H-imidazol-5-yl]-2-(2-thienyl)methyl-2-propenoic acid;

or a pharmaceutically acceptable salt thereof.

5. A pharmaceutical composition comprising a pharmaceutical carrier and a compound of claim 1.

6. A method of antagonizing angiotensin II receptors which comprises administering to a subject in need thereof an effective amount of claim 1.

7. A method of treating hypertension which comprises administering to a subject in need thereof an effective amount of a compound of claim 1.

8. A method of treating congestive heart failure which comprises administering to a subject in need thereof an effective amount of a compound of claim 1.

9. A method of treating renal failure which comprises administering to a subject in need thereof an effective amount of a compound of claim 1.

10. A method of treating glaucoma which comprises administering to a subject in need thereof an effective amount of a compound of claim 1.

* * * * *